US012605324B2

(12) United States Patent
Hamazaki et al.

(10) Patent No.: US 12,605,324 B2
(45) Date of Patent: Apr. 21, 2026

(54) COMPOSITION COMPRISING INGREDIENTS FOR DIC-GEL AND POLYOL

(71) Applicant: L'OREAL, Paris (FR)

(72) Inventors: Tomomi Hamazaki, Kawasaki (JP); Toru Koike, Kawasaki (JP); Nozomi Takahashi, Kawasaki (JP); Takehiko Kasai, Kawasaki (JP); Tatsushi Isojima, Kawasaki (JP); Toshifumi Shiroya, Kawasaki (JP); Hidehiko Asanuma, Kawasaki (JP)

(73) Assignee: L'Oreal, Paris (FR)

(*) Notice: Subject to any disclaimer, the term of this patent is extended or adjusted under 35 U.S.C. 154(b) by 738 days.

(21) Appl. No.: 17/622,607

(22) PCT Filed: Jun. 2, 2020

(86) PCT No.: PCT/JP2020/022453
§ 371 (c)(1),
(2) Date: Dec. 23, 2021

(87) PCT Pub. No.: WO2020/261950
PCT Pub. Date: Dec. 30, 2020

(65) Prior Publication Data

US 2022/0362128 A1 Nov. 17, 2022

(30) Foreign Application Priority Data

Jun. 27, 2019 (JP) ................................ 2019-119924

(51) Int. Cl.

| | |
|---|---|
| ***A61K 8/73*** | (2006.01) |
| ***A61K 8/04*** | (2006.01) |
| ***A61K 8/55*** | (2006.01) |
| ***A61Q 17/04*** | (2006.01) |

(52) U.S. Cl.
CPC .............. *A61K 8/731* (2013.01); *A61K 8/042* (2013.01); *A61K 8/55* (2013.01); *A61Q 17/04* (2013.01); *A61K 2800/95* (2013.01)

(58) Field of Classification Search
None
See application file for complete search history.

(56) References Cited

U.S. PATENT DOCUMENTS

2009/0041711 A1* 2/2009 Molenda .................. A61Q 5/12
424/70.12

FOREIGN PATENT DOCUMENTS

| | | | | | |
|---|---|---|---|---|---|
| CN | 105250148 | A | | 1/2016 | |
| CN | 108366915 | A | | 8/2018 | |
| CN | 108367175 | A | | 8/2018 | |
| EP | 2005942 | A1 | * | 12/2008 | ............. A61K 8/046 |
| JP | 2005-015359 | A | | 1/2005 | |
| JP | 2006-083140 | A | | 3/2006 | |
| JP | 2014227389 | A | | 12/2014 | |
| JP | 2015143213 | A | * | 8/2015 | |
| KR | 10-2010-0013719 | A | | 2/2010 | |
| WO | WO-9637187 | A1 | * | 11/1996 | ......... A61K 31/6615 |
| WO | 2007/127987 | A2 | | 11/2007 | |
| WO | 2013153678 | A1 | | 10/2013 | |
| WO | 2018230740 | A1 | | 12/2018 | |
| WO | 2019116877 | A1 | | 6/2019 | |
| WO | 2020045134 | A1 | | 3/2020 | |

OTHER PUBLICATIONS

GNPD MINTEL: "Purifying Clay Cleanser", May 12, 2016, XP055726853, retrieved from www.gnpd.com, database accession No. 3992245; see IDS filed Dec. 23, 2021 (Year: 2016).*
GNPD MINTEL: "Restorative Anti-Aging Eye Cream", Jan. 2019, XP055726891, retrieved from www.gnpd.com, database accession No. 6281913; see IDS filed Dec. 23, 2021 (Year: 2019).*
Machine translation, Description, WO 96/37187 A1 (2025).*
Bharate, S., Enhancing Biopharmaceutical Attributes of Khellin by Amorphous Binary Solid Dispersions, AAPS PharmSciTech Oct. 27, 2021;22(8):260 (Year: 2021).*
Machine translation of Description, JP 2015143213A (2025).*
International Search Report mailed Sep. 10, 2020, issued in corresponding International Application No. PCT/JP2020/022453, filed Jun. 2, 2020, 3 pages.
GNPD MINTEL: "Restorative Anti-Aging Eye Cream", Jan. 25, 2019, XP055726891, retrieved from www.gnpd.com, database accession No. 6281913.
GNPD MINTEL: "Purifying Clay Cleanser", May 12, 2016, XP055726853, retrieved from www.gnpd.com, database accession No. 3992245.
Third Party Observation issued Nov. 7, 2022 in corresponding Japanese Application No. 2019-119924, filed Jun. 27, 2019, 7 pages.
Office Action mailed Apr. 22, 2023, issued in corresponding Chinese Application No. 202080046073.8, filed Jun. 2, 2020, 18 pages.
European Opposition mailed May 8, 2025, issued in European Patent Application No. 20746730.9, filed Jun. 2, 2020, 21 pages.
Korean Notice of Allowance mailed Nov. 24, 2025, issued in corresponding Korean Application No. KR10-2021-7042102, filed Dec. 22, 2021, 5 pages.

* cited by examiner

*Primary Examiner* — H. Sarah Park
(74) *Attorney, Agent, or Firm* — CHRISTENSEN O'CONNOR JOHNSON KINDNESS PLLC

(57) ABSTRACT

The present invention relates to a composition comprising, in at least one physiologically acceptable volatile medium: (a) at least one cationic polysaccharide; (b) at least one crosslinker having three or more acid groups or a salt thereof; (c) at least one powder; and (d) at least one polyol, wherein the (c) powder is insoluble in the physiologically acceptable volatile medium. The composition can form a film including a DIC-gel and a powder wherein the distribution of the powder in the film can be more even or more uniform.

12 Claims, No Drawings

COMPOSITION COMPRISING INGREDIENTS FOR DIC-GEL AND POLYOL

TECHNICAL FIELD

The present invention relates to a composition including a dynamically and ionically-crosslinked (DIC) gel.

BACKGROUND ART

A polyion complex which is formed with an anionic polymer and a cationic polymer has already been known.

In order to prepare the polyion complex, typically, an aqueous solution of an anionic polymer and another aqueous solution of a cationic polymer can be mixed. By changing the pH of the mixture thus obtained, the anionic and cationic polymers are ionically bonded to form gel particles under a specific pH condition. The gel particles can form insoluble water resistance films by offsetting the electric charges of the anionic and cationic polymers.

The use of a film made from a polyion complex for cosmetic purposes is also proposed in, for example, WO 2013/153678 and JP-A-2014-227389. The film disclosed in WO 2013/153678 and JP-A-2014-227389 can provide certain cosmetic effects.

It has been discovered that a dispersion including a polyion complex is not always stable. In particular, a dispersion including a polyion complex tends to be unstable at an elevated temperature such as 45° C. or more. If the dispersion is unstable, the polyion complex tends to precipitate, and therefore, the dispersion can cause phase separation.

In order to improve the stability of a dispersion including a polyion complex, it has also been discovered that the use of at least one cationic polysaccharide is effective. For example, as the cationic polymer, a cationic polysaccharide may be used. Alternatively, a cationic polysaccharide may be added to a combination of an anionic polymer and a cationic polymer.

DISCLOSURE OF INVENTION

As a result of further research, it has been discovered that only at least one cationic polysaccharide can be used with at least one crosslinker having three or more acid groups or salt thereof to form a gel which is a dynamically and ionically-crosslinked gel, which is abbreviated as a DIC-gel. The DIC-gel which is preferably in the form of particles can also form insoluble water resistance films.

However, it has also been discovered that if the film formed by a DIC-gel includes a powder, the distribution of the powder in the film may be less even or less uniform. Thus, if the powder has color such as white, the color of the film may be uneven or non-uniform. Also, if the powder can function as a UV filter, the UV shielding effects due to the powder may be exhibited less evenly or less uniformly, and therefore, some parts of the film may not be able to effectively shield UV rays while the other parts of the film may be able to effectively shield UV rays, which can reduce the entire SPF value of the film.

Thus, an objective of the present invention is to provide a composition which can form a film including a DIC-gel and a powder wherein the distribution of the powder in the film can be more even or more uniform.

In particular, the present invention aims to provide a composition which can form a film including a DIC-gel and a powder wherein the properties or effects, such as color and UV shielding, due to the powder can be exhibited more evenly or more uniformly from the surface of the film, which may result in, for example, a more even or more uniform color and/or an increase in the entire SPF value of the film.

The above objective of the present invention can be achieved by a composition comprising, in at least one physiologically acceptable volatile medium:

(a) at least one cationic polysaccharide;

(b) at least one crosslinker having three or more acid groups or a salt thereof;

(c) at least one powder; and (d) at least one polyol, wherein the (c) powder is insoluble in the physiologically acceptable volatile medium.

The (a) cationic polysaccharide may be selected from cationic cellulose polymers.

The (a) cationic polysaccharide may have at least one quaternary ammonium group.

The (a) cationic polysaccharide may be selected from the group consisting of polyquaternium-4, polyquaternium-10, polyquaternium-24, polyquatemium-67, and a mixture thereof.

The amount of the (a) cationic polysaccharide(s) in the composition according to the present invention may be from 0.01% to 10% by weight, preferably from 0.05% to 5% by weight, and more preferably from 0.1% to 1% by weight, relative to the total weight of the composition.

The (b) crosslinker having three or more acid groups or a salt thereof may be selected from non-polymeric organic acids having three or more acid groups and salts thereof.

The (b) crosslinker having three or more acid groups may have three or more acid groups selected from the group consisting of a carboxylic group, a sulfuric group, a sulfonic group, a phosphonic group, phosphoric group, a phenolic hydroxyl group, and a mixture thereof.

The (b) crosslinker having three or more acid groups or a salt thereof may be selected from the group consisting of phytic acid, citric acid, aconitic acid, EDTA, glycyrrhizin, inositol triphosphate, inositol pentakisphosphate, tripolyphosphate, adenosine triphosphate, a salt thereof, and a mixture thereof.

The amount of the (b) crosslinker(s) having three or more acid groups or a salt(s) thereof in the composition according to the present invention may be from 0.001% to 10% by weight, preferably from 0.05% to 5% by weight, and more preferably from 0.1% to 1% by weight, relative to the total weight of the composition.

The (c) powder may be selected from pigments, fillers, UV filters and mixtures thereof, preferably from inorganic pigments, inorganic fillers, UV filters and mixtures thereof, and more preferably from titanium dioxide particles, silica particles and mixtures thereof.

The amount of the (c) powder(s) in the composition according to the present invention may be from 0.1% to 25% by weight, preferably from 0.5% to 20% by weight, and more preferably from 1% to 15% by weight, relative to the total weight of the composition.

The (d) polyol may be selected from the group consisting of glycerin, ethyleneglycol, polyethyleneglycol, propyleneglycol, dipropyleneglycol, butyleneglycol, pentyleneglycol, hexyleneglycol and mixtures thereof.

The amount of the (d) polyol(s) in the composition according to the present invention may be from 0.1% to 20% by weight, preferably from 0.5% to 15% by weight, and more preferably from 1% to 10% by weight, relative to the total weight of the composition.

The composition according to the present invention may be a cosmetic composition, preferably a skin cosmetic composition.

The present invention also relates to a cosmetic process for a keratin substance such as skin, comprising applying to the keratin substance the composition according to the present invention, and drying the composition to form a cosmetic film on the keratin substance.

BEST MODE FOR CARRYING OUT THE INVENTION

After diligent research, the inventors have discovered that it is possible to provide a composition which can form a film including a DIC-gel and a powder wherein the distribution of the powder in the film can be more even or more uniform.

Thus, the composition according to the present invention comprises, in at least one physiologically acceptable volatile medium:

(a) at least one cationic polysaccharide;

(b) at least one crosslinker having three or more acid groups or a salt thereof;

(c) at least one powder; and (d) at least one polyol, wherein the (c) powder is insoluble in the physiologically acceptable volatile medium.

Surprisingly, the use of the (d) polyol(s) with a combination of the (a) cationic polysaccharide(s) and the (b) crosslinker having three or more acid groups or a salt thereof, which form a DIC-gel, can improve the distribution of the (c) powder in the film formed by the composition according to the present invention. Thus, the distribution of the (c) powder in the film can be more even or more uniform, as compared to the case in which no polyol is used with a combination of the ingredients (a) and (b).

In particular, the present invention can provide a composition which can form a film including a DIC-gel and a powder wherein the properties or effects, such as color and UV shielding, due to the powder can be exhibited more evenly or more uniformly from the surface of the film. For example, the film formed by the composition according to the present invention can have a more even color along the surface of the film and a higher SPF value for the entire surface of the film, as compared to the case in which no polyol is used under a combination of the ingredients (a) and (b). Thus, the film can show a more homogeneous color and/or more improved total UV shielding effects represented by the SPF value of the film.

The present invention can also provide additional effects.

The composition according to the present invention can provide a self-healing or self-repairing film. In other words, the film provided by the composition according to the present invention can be automatically repaired even though the film is broken due to, for example, scratching and the like, and therefore, long lastingness of cosmetic effects provided by the film can be improved.

The self-healing or self-repairing film can be composed of a gel, preferably a hydrogel. The gel is dynamically and ionically-crosslinked. The dynamically and ionically-crosslinked gel prepared by the composition according to the present invention is a DIC-gel.

The dynamic and ionic-crosslinking in the DIC-gel is different from permanent covalent bonding because it is breakable but reformable. The dynamic and ionic-crosslinking can be easily broken by, for example, cutting and the like, but can be easily reformed by, for example, contacting each other, thereby exhibiting self-healing or self-repairing properties. For example, if the gel is cut into two pieces, the ionic interaction between the cationic polymer and the crosslinker breaks. However, if the two pieces contact each other, they can reform the ionic-bonding between the cationic polymer and the crosslinker, and they can adhere to each other. Therefore, even if cracks, for example, are formed on the gel, they can disappear.

The composition according to the present invention is stable for a long period of time, and can be used to easily prepare a film of a gel which has self-healing or self-repairing properties by applying the composition onto a substrate, preferably a keratin substance such as skin, and drying the composition.

The film prepared by the composition according to the present invention can have a variety of cosmetic functions.

For example, the film itself prepared by the composition according to the present invention may have cosmetic effects such as absorbing or adsorbing malodor, changing the appearance of a keratin substance such as skin, changing the feel to the touch of the keratin substance, and/or protecting the keratin substance from, for example, dirt or pollutants.

Since the film prepared by the composition according to the present invention includes at least one powder, the film can have cosmetic effects provided by the powder(s). For example, if the film includes at least one powder having color and/or UV shielding effects, the film can cover or conceal the original color of a keratin substance such as skin and/or protect the keratin substance from UV rays. Further, the film can exhibit long-lasting coloring and/or long-lasting UV shielding effects. Furthermore, the film can even increase the SPF value by providing mechanical power by, for example, friction to the film, because the distribution of the powder in the film can be rearranged by the mechanical power to be more homogeneous without breaking the film.

Hereinafter, the composition, process and the like according to the present invention will be explained in a more detailed manner.

[Cationic Polysaccharide]

The composition according to the present invention includes (a) at least one cationic polysaccharide. Two or more different types of (a) cationic polysaccharides may be used in combination. Thus, a single type of (a) cationic polysaccharide or a combination of different types of (a) cationic polysaccharides may be used.

The (a) cationic polysaccharide has a positive charge density. The charge density of the (a) cationic polysaccharide may be from 0.01 meq/g to 20 meq/g, preferably from 0.05 to 15 meq/g, and more preferably from 0.1 to 10 meq/g.

It may be preferable that the molecular weight of the (a) cationic polysaccharide be 500 or more, preferably 1,000 or more, more preferably 2,000 or more, and even more preferably 5,000 or more.

Unless otherwise defined in the description, "molecular weight" means a number average molecular weight.

The (a) cationic polysaccharide may have at least one positively chargeable and/or positively charged moiety selected from the group consisting of a primary, secondary or tertiary amino group, a quaternary ammonium group, a guanidine group, a biguanide group, an imidazole group, an imino group, and a pyridyl group. The term (primary) "amino group" here means the group —$NH_2$. It is preferable that the (a) cationic polysaccharide have at least one quaternary ammonium group.

The (a) cationic polysaccharide may be a homopolymer or a copolymer. The term "copolymer" is understood to mean both copolymers obtained from two kinds of monomers and those obtained from more than two kinds of monomers, such as terpolymers obtained from three kinds of monomers.

The (a) cationic polysaccharide may be selected from natural and synthetic cationic polysaccharides.

It is preferable that the (a) cationic polysaccharide be selected from cationic cellulose polymers. Non-limiting examples of the cationic cellulose polymers are as follows.

(1) Cationic cellulose polymers such as cellulose ether derivatives comprising one or more quaternary ammonium groups described, for example, in French Patent No. 1 492 597, such as the polymers sold under the names "JR" (JR 400, JR 125, JR 30M) or "LR" (LR 400, LR 30M) by the company Dow Chemical. These polymers are also defined in the CTFA dictionary as quaternary ammoniums of hydroxyethylcellulose that have reacted with an epoxide substituted with a trimethylammonium group.

(2) Cationic cellulose polymers such as cellulose copolymers and cellulose derivatives grafted with at least one water-soluble monomer of quaternary ammonium, and described, for example, in U.S. Pat. No. 4,131,576, such as hydroxyalkylcelluloses, for instance, hydroxymethyl-, hydroxyethyl-, and hydroxypropylcelluloses grafted, for example, with at least one chosen from methacryloylethyltrimethylammonium, methacrylamidopropyltrimethylammonium, and dimethyldiallylammonium. Commercial products corresponding to these polymers include, for example, the products sold under the names "Celquat® L 200" and "Celquat® H 100" by the company Akzo Novel.

(3) Cationic cellulose polymers having at least one quaternary ammonium group comprising at least one fatty chain, such as alkyl, arylalkyl or alkylaryl groups comprising at least 8 carbon atoms. It may be preferable that the cationic cellulose polymers be quaternized hydroxyethyl celluloses modified with at least one quaternary ammonium group comprising at least one fatty chain, such as alkyl, arylalkyl or alkylaryl groups comprising at least 8 carbon atoms, or mixtures thereof. The alkyl radicals borne by the quaternary ammonium group may preferably contain from 8 to 30 carbon atoms, especially from 10 to 30 carbon atoms. The aryl radicals preferably denote phenyl, benzyl, naphthyl or anthryl groups. More preferably, the cationic cellulose polymer may comprise at least one quaternary ammonium group including at least one $C_8$-$C_{30}$ hydrocarbon group. Examples of quaternized alkylhydroxyethylcelluloses containing $C_8$-$C_{30}$ fatty chains that may be mentioned include the products Quatrisoft LM 200, Quatrisoft LM-X 529-18-A, Quatrisoft LM-X 529-18B (C12 alkyl) and Quatrisoft LM-X 529-8 (C18 alkyl) or Softcat Polymer SL100, Softcat SX-1300X, Softcat SX-1300H, Softcat SL-5, Softcat SL-30, Softcat SL-60, Softcat SK-MH, Softcat SX-400X, Softcat SX-400H, SoftCat SK-L, Softcat SK-M, and Softcat SK-H, sold by the company Dow Chemical, and the products Crodacel QM, Crodacel, QL (C12 alkyl) and Crodacel QS (C18 alkyl) sold by the company Croda.

It is preferable that the (a) cationic polysaccharide be selected from the group consisting of polyquaternium-4, polyquaternium-10, polyquaternium-24, polyquaternium-67, and a mixture thereof.

The amount of the (a) cationic polysaccharide(s) in the composition according to the present invention may be 0.01% by weight or more, preferably 0.05% by weight or more, and more preferably 0.1% by weight or more, relative to the total weight of the composition.

The amount of the (a) cationic polysaccharide(s) in the composition according to the present invention may be 10% by weight or less, preferably 5% by weight or less, and more preferably 1% by weight or less, relative to the total weight of the composition.

The amount of the (a) cationic polysaccharide(s) in the composition according to the present invention may be from 0.01% to 10% by weight, preferably from 0.05% to 5% by weight, and more preferably from 0.1% to 1% by weight, relative to the total weight of the composition.

[Crosslinker]

The composition according to the present invention includes (b) at least one crosslinker having three or more acid groups or a salt thereof. Two or more different types of (b) crosslinkers or salts thereof may be used in combination. Thus, a single type of (b) crosslinker or a salt thereof or a combination of different types of (b) crosslinkers or salts thereof may be used.

At least one of the acid groups of the (b) crosslinker having three or more acid groups may be in the form of a salt. All the acidgroups of the (b) crosslinker may be in the form of salts.

The term "salt" in the present specification means a salt formed by addition of a suitable base(s) to the (b) crosslinker having three or more acid groups, which may be obtained from a reaction with the (b) crosslinker having three or more acid groups with the base(s) according to the methods known to those skilled in the art. As the salt, mention may be made of metal salts, for example salts with an alkaline metal such as Na and K, and salts with an alkaline earth metal such as Mg and Ca, and ammonium salts.

It is preferable that the (b) crosslinker be selected from non-polymeric acids having three or more acid groups, more preferably from non-polymeric organic acids having three or more acid groups.

The term "non-polymeric" here means that the (b) crosslinker is not obtained by polymerizing two or more monomers. Therefore, the non-polymeric acid, in particular the non-polymeric organic acid, does not correspond to an acid obtained by polymerizing two or more monomers such as polycarboxylic acid.

It is preferable that the molecular weight of the non-polymeric acid, in particular the non-polymeric organic acid, having three or more acid groups be 1000 or less, preferably 800 or less, and more preferably 600 or less.

The (b) crosslinker having three or more acid groups, or a salt thereof, may be hydrophilic or water-soluble.

The (b) crosslinker having three or more acid groups may have three or more acid groups selected from the group consisting of a carboxylic group, a sulfuric group, a sulfonic group, a phosphonic group, a phosphoric group, a phenolic hydroxyl group, and a mixture thereof.

The (b) crosslinker having three or more acid groups or a salt thereof may be selected from the group consisting of tricarboxylic acids, tetracarboxylic acids, pentacarboxylic acids, hexacarboxylic acids, salts thereof, and mixtures thereof.

The (b) crosslinker having three or more acid groups or a salt thereof may be selected from the group consisting of citric acid, aconitic acid, phytic acid, EDTA, glycyrrhizin, inositol triphosphate, inositol pentakisphosphate, tripolyphosphate, adenosine triphosphate, a salt thereof, and a mixture thereof.

It may be preferable that the (b) crosslinker having three or more acid groups or salt thereof be selected from the group consisting of citric acid, phytic acid, a salt thereof, and a mixture thereof.

The amount of the (b) crosslinker(s) having three or more acid groups or a salt(s) thereof in the composition according to the present invention may be 0.001% by weight or more, preferably 0.05% by weight or more, and more preferably 0.1% by weight or more, relative to the total weight of the composition.

The amount of the (b) crosslinker(s) having three or more acid groups or a salt(s) thereof in the composition according to the present invention may be 10% by weight or less, preferably 5% by weight or less, and more preferably 1% by weight or less, relative to the total weight of the composition.

The amount of the (b) crosslinker(s) having three or more acid groups or a salt(s) thereof in 50 the composition according to the present invention may be from 0.001% to 10% by weight, preferably from 0.05% to 5% by weight, and more preferably from 0.1% to 1% by weight, relative to the total weight of the composition.

[Physiologically Acceptable Volatile Medium]

The composition according to the present invention includes at least one physiologically acceptable volatile medium.

The term "physiologically acceptable" volatile medium is intended to denote a volatile medium that is particularly suitable for applying the composition according to the present invention to a keratin substance(s).

The term "volatile" means that the physiologically acceptable medium can evaporate under normal atmospheric pressure such as 1 atm and at room temperature such as 25° C.

The physiologically acceptable medium is generally adapted to the nature of the support onto which the composition according to the present invention is to be applied, and also to the form in which the composition according to the present invention is to be packaged.

The physiologically acceptable volatile medium may comprise or consist of at least one hydrophilic organic solvent, water or a mixture thereof. It is preferable that the physiologically acceptable volatile medium comprise water or consist of water.

As the hydrophilic organic solvent, mention may be made of, for example, monoalcohols containing from 2 to 6 carbon atoms, such as ethanol or isopropanol.

The amount of the physiologically acceptable volatile medium, preferably water, in the composition according to the present invention may be 30% by weight or more, preferably 40% by weight or more, and more preferably 50% by weight or more, relative to the total weight of the composition.

The amount of the physiologically acceptable volatile medium, preferably water, in the composition according to the present invention may be 90% by weight or less, preferably 80% by weight or less, and more preferably 70% by weight or less, relative to the total weight of the composition.

The amount of the physiologically acceptable volatile medium, preferably water, in the composition according to the present invention may be from 30% to 90% by weight, preferably from 40% to 80% by weight, and more preferably from 50% to 70% by weight, relative to the total weight of the composition.

[Powder]

The composition according to the present invention includes (c) at least one powder. Two or more different types of (c) powders may be used in combination. Thus, a single type of (c) powder or a combination of different types of (c) powders may be used.

According to the present invention, the (c) powder is insoluble in the physiologically acceptable volatile medium.

For the purposes of the present invention, the term "insoluble" powder means a powder with a solubility in the physiologically acceptable volatile medium such as water at 25° C. of less than 1% by weight, preferably less than 0.1% by weight and more preferably less than 0.01% by weight, relative to the total weight of the powder, and most preferably with no solubility.

The (c) powder is in the form of a particle or particles.

The diameter of the (c) powder is not limited. The average particle size of the (c) powder is preferably 10 nm or more, more preferably 50 nm or more, and even more preferably 100 nm or more, and is preferably 1000 μm or less, more preferably 500 μm or less, and even more preferably 300 μm or less. Thus, the (c) powder may have an average particle size of from 10 nm to 1000 μm, preferably from 50 nm to 500 μm, and more preferably from 100 nm to 300 nm. The average particle size may be number-average particle size which can be measured by dynamic light scattering with, for example, Nicomp Z380.

The (c) powder is preferably in the form of a solid.

The (c) powder may be selected from pigments, fillers, UV filters, and mixtures thereof.

(Pigment)

The term "pigments" should be understood as meaning white or colored and inorganic or organic particles which are insoluble in the physiologically acceptable volatile medium and which are intended to color and/or opacify the resulting film.

The pigments preferably have an absorption ranging from 380 to 780 nm, and in at least one embodiment, an absorption with a maximum in this absorption range.

The pigments may be organic pigments. As used herein, the term "organic pigment" means any pigment that satisfies the definition in Ullmann's encyclopedia in the chapter on organic pigments. The organic pigment may be chosen, for example, from nitroso, nitro, azo, xanthene, quinoline, anthraquinone, phthalocyanin, metal complex, isoindolinone, isoindoline, quinacridone, perinone, perylene, diketopyrrolopyrrole, thioindigo, dioxazine, triphenylmethane, and quinophthalone compounds.

The at least one organic pigment may be chosen, for example, from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21100, 21108, 47000, and 47005, the green pigments codified in the Color Index under the references CI 61565, 61570, and 74260, the orange pigments codified in the Color Index under the references CI 11725, 15510, 45370, and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, and 75470, and the pigments obtained by oxidative polymerization of indole or phenolic derivatives as described, for example, in French Patent No. 2 679 771.

These pigments may also be in the form of composite pigments as described, for example, in European Patent No. 1 184 426. These composite pigments may be composed, for instance, of particles comprising an inorganic nucleus at least partially coated with an organic pigment and at least one binder to fix the organic pigments to the nucleus.

Other examples may include pigmentary pastes of organic pigments such as the products sold by the company Hoechst under the names: Jaune Cosmenyl IOG: Pigment Yellow 3 (CI 11710); Jaune Cosmenyl G: Pigment Yellow 1 (CI 11680); Orange Cosmenyl GR: Pigment Orange 43 (CI 71105); Rouge Cosmenyl R": Pigment Red 4 (CI 12085); Carmine Cosmenyl FB: Pigment Red 5 (CI 12490); Violet Cosmenyl RL: Pigment Violet 23 (CI 51319); Bleu Cosmenyl A2R: Pigment Blue 15.1 (CI 74160); Vert Cosmenyl GG: Pigment Green 7 (CI 74260); and Noir Cosmenyl R: Pigment Black 7 (CI 77266).

The at least one pigment may also be chosen from lakes. As used herein, the term "lake" means insolublized dyes adsorbed onto insoluble particles, the complex or the compound thus obtained remaining insoluble during use.

The inorganic substrates onto which the dyes are adsorbed may include, for example, alumina, silica, calcium sodium borosilicate, calcium aluminum borosilicate, and aluminum.

Non-limiting examples of organic dyes include cochineal carmine and the products known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), and D&C Blue 1 (CI 42 090).

An additional non-limiting example of a lake is the product known under the following name: D&C Red 7 (CI 15 850:1).

The at least one pigment may also be a pigment with special effects. As used herein, the term "pigments with special effects" means pigments that generally create a non-uniform colored appearance (characterized by a certain shade, a certain vivacity, and/or a certain lightness) that changes as a function of the conditions of observation (light, temperature, observation angles, etc.). They thus contrast with white or colored pigments that afford a standard uniform opaque, semi-transparent, or transparent shade.

Two types of pigment with special effects exist: those with a low refractive index, such as fluorescent, photochromic, and thermochromic pigments, and those with a high refractive index, such as nacres and flakes.

The at least one pigment may also be chosen from pigments with an interference effect that are not fixed onto a substrate, for instance, liquid crystals (Helicones HC from Wacker), and holographic interference flakes (Geometric Pigments or Spectra f/x from Spectratek).

The pigments with special effects may also comprise fluorescent pigments, whether these are substances that are fluorescent in daylight or that produce an ultraviolet fluorescence, phosphorescent pigments, photochromic pigments, and thermochromic pigments.

The pigment may also be an inorganic pigment, in a preferred embodiment. As used herein, the term "inorganic pigment" means any pigment that satisfies the definition in Ullmann's encyclopedia in the chapter on inorganic pigments. Preferably, the inorganic pigments comprise at least one inorganic material. Non-limiting examples of inorganic pigments that are useful in the present invention include metal oxides, in particular, transition metal oxides, such as zirconium oxides, cerium oxides, iron oxides, zinc oxides, chromium oxides, manganese violet, ultramarine blue, chromium hydrate, ferric blue, and titanium dioxide. The following inorganic pigments may also be used: $Ta_2O_5$, $Ti_3O_5$, $Ti_2O_3$, TiO, and $ZrO_2$ as a mixture with $TiO_2$, $ZrO_2$, $Nb_2O_5$, $CeO_2$, and ZnS.

The pigment may also be a nacreous pigment such as a white nacreous pigment, for example, mica coated with titanium or with bismuth oxychloride, a colored nacreous pigment such as mica coated with titanium and with iron oxides, mica coated with titanium and, for example, with ferric blue or chromium oxide, mica coated with titanium and with an organic pigment as defined above, and also a nacreous pigment based on bismuth oxychloride. Examples of such pigments may include the Cellini pigments sold by Engelhard (Mica-$TiO_2$-lake), Prestige sold by Eckart (Mica-$TiO_2$), and Colorona sold by Merck (Mica-$TiO_2$.$Fe_2O_3$).

In addition to nacres on a mica support, multilayer pigments based on synthetic substrates such as alumina, silica, calcium sodium borosilicate, calcium aluminum borosilicate, and aluminum, may be useful in accordance with the present disclosure.

(Filler)

The term "filler" should be understood as meaning an uncolored particle that is solid at room temperature and atmospheric pressure, and insoluble in the physiologically acceptable volatile medium, even when these ingredients are brought to a temperature above room temperature.

Of inorganic or organic nature thereof, fillers make it possible to confer firmness on the composition according to the present invention and/or softness and uniformity on the make-up which may be formed by the composition.

The filler may be chosen from mineral and organic fillers. When the fillers are organic fillers, they are polymeric organic fillers. The filler may be particles of any form, for example, platelet-shaped, spherical, and oblong, irrespective of their crystallographic form (for example lamellar, cubic, hexagonal, and orthorhombic).

The fillers that may be used in the composition according to the present invention can be made from various inorganic and/or organic materials, and may include, but are not limited to, titanium dioxide; talc; natural or synthetic mica; alumina; aluminosilicate; silica (or silicon dioxides); kaolin or other insoluble silicates such as clays; polyamides (Nylon®), poly-β-alanine and polyethylene powders; tetrafluoroethylene polymer (Teflon®) powders, powder starch; boron nitride; acrylic acid polymer powders; silicone resin microbeads, for instance "Tospearls®" from the company Toshiba; bismuth oxychlorides; precipitated calcium carbonate; magnesium carbonate and magnesium hydrogen carbonate; hydroxyapatite; hollow silica microspheres such as "Silica Beads SB 700®" and "Silica Beads SB 700®" from the company Maprecos, "Sunspheres H-33®" and "Sunspheres H-51®" from the company Asahi Glass; acrylic polymer microspheres such as those made from crosslinked acrylate copolymer "Polytrap 6603®" from the company R.P. Scherrer and those made from polymethyl methacrylate "Micropearl M100®" from the company SEPPIC; polyurea powders; polyurethane powders such as the hexamethylene diisocyanate and trimethylol hexyl lactone copolymer powder sold under the name "Plastic Powder D-400®" by the company Toshiki; glass or ceramic microcapsules; microcapsules of methyl acrylate or methacrylate polymers or copolymers, or alternatively, vinylidene chloride and acrylonitrile copolymers, for instance, "Expancel®" from the company Expancel; elastomeric crosslinked organopolysiloxane powders such as those sold under the name "KSP100®" by the company Shinetsu Chemical; porous cellulose beads such as those sold under the name of Cellulose Beads USF® by the company Daito Kasei; and mixtures thereof.

Among the silicas that are useful in the composition of the present invention, mention may be made of crystalline, microcrystalline and non-crystalline silicas.

By way of example, crystalline silicas that may be mentioned include quartz, tridymite, cristobalite, keatite, coesite and stishovite. The microcrystalline silicas are, for example, diatomite.

Among the non-crystalline forms that may be used are vitreous silica and other types of amorphous silicas such as colloidal silicas, silica gels, precipitated silicas and fumed silicas, for instance aerosils, and pyrogenic silicas. Porous silica such as an aerogel (silica silylate) is preferable.

In one embodiment of the present invention, the (c) powder may comprise at least one inorganic material selected from the group consisting of talc, mica, silica, kaolin, sericite, calcinated talc, calcinated mica, calcinated sericite, synthetic mica, bismuth oxychloride, barium sulfate, boron nitride, calcium carbonate, magnesium carbonate, magnesium hydrogen carbonate, and hydroxyapatite. The (c) powder may comprise selenium disulfide.

In another embodiment of the present invention, the (c) powder may comprise at least one organic material selected from the group consisting of polyurea, melamine-formaldehyde condensate, urea-formaldehyde condensate, aminoplast, polyurethane, polyacrylate, polyphosphate, polystyrene, polyester, polyamide, polyolefin, polysaccharide, silicone, silicone resin, protein, modified cellulose, and gum.

(Surface Treatment)

According to the present invention, the (c) powder may be surface treated. The surface treatment can be performed by any conventional process.

For the purposes of the present invention, the surface treatment is such that, for instance, a surface-treated powder conserves its intrinsic pretreatment pigmenting properties and a surface-treated filler conserves its intrinsic pretreatment filling properties. For example, inorganic substrates such as alumina and silica onto which organic dyes are adsorbed are preferably not surface-treated fillers for the purposes of the present invention.

The (c) powder may have at least one hydrophobic coating.

The hydrophobic coating may be formed by treating the (c) powder with a hydrophobic treating agent. The hydrophobic treating agent can be chosen from silicones, such as methicones, dimethicones or perfluoroalkylsilanes; fatty acids, such as stearic acid; perfluoroalkyl phosphates, perfluoroalkylsilanes, perfluoroalkylsilazanes, poly(hexafluoropropylene oxides), polyorganosiloxanes comprising perfluoroalkyl or perfluoropolyether groups, and amino acids; N-acylated amino acids or their salts; lecithin, isopropyl triisostearyl titanate, and their mixtures.

As the (c) powder, silicone-treated silica beads can be used.

As the (c) powder, $TiO_2$ particles coated with at least one hydrophobic coating can also be used. Among the coated $TiO_2$ particles, mention may be made of:

those coated with polydimethylsiloxane (CARDRE ULTRAFINE TITANIUM DIOXIDE AS provided by the company CARDRE);

those coated with polymethylhydrogenosiloxane (untreated titanium oxide coated with polymethylhydrogenosiloxane sold under the trade name Cosmetic White SA-$C_{47-05}$1-10 by the company MYOSHI);

those coated with perfluoropolymethyl isopropyl ether (CARDRE MICA FHC 70173 OR 70170 CARDRE UF TIO2 FHC provided by the company CARDRE);

those coated with silica (SPHERITITAN AB provided by the company CATALYSTS & CHEMICALS;

those coated with teflon (CS-13997 TEFLON COATED TITANIUM DIOXIDE provided by the company CLARK COLORS); and those coated with polyester (EXPERIMENTAL DESOTO BEADS provided by the company DESOTO).

Among these $TiO_2$ treated particles, $TiO_2$ particles coated with silicone such as polydimethylsiloxane are more preferable.

According to one embodiment of the present invention, the (c) powder may be surface treated with at least one amphiphilic agent, in particular, the (c) powder may be partially or fully surface treated with at least one amphiphilic agent. It is preferable that the (c) powder is partially treated with the amphiphilic agent(s). The (c) powder may be located between a continuous phase and a dispersed phase of the composition according to the present invention, if it has these phases, to form a Pickering emulsion. The dispersed phases preferably connect with each other via the particles.

The amphiphilic agent can provide the (c) powder with both hydrophilic and hydrophobic properties. Preferably, the (c) powder has an amphiphilic surface.

The amphiphilic agent may comprise at least one compound chosen from, for example, amino acids; fatty acids, fatty alcohols and derivatives thereof, such as stearic acid, hydroxystearic acid, stearyl alcohol, hydroxystearyl alcohol, lauric acid, and derivatives thereof; anionic surfactants; lecithins; sodium, potassium, magnesium, iron, titanium, zinc, or aluminum salts of fatty acids, for example, aluminum stearate or laurate; metal alkoxides; polysaccharides, for example, chitosan, cellulose, and derivatives thereof; polyethylenes; (meth)acrylic polymers, for example, polymethyl methacrylates; polymers and copolymers containing acrylate units; proteins; and alkanolamines.

The (c) powder may be surface treated with a mixture of amphiphilic agents, and/or may be subjected to several surface treatments with amphiphilic agents.

The surface-treated powder may be prepared according to surface-treatment techniques that are well known to those skilled in the art, or may be commercially available in the required form.

Preferably, the surface-treated powder is coated with an organic layer. The organic layer may be deposited on the powder by evaporation of a solvent, chemical reaction between the molecules in the amphiphilic agents, or creation of a covalent bond between the molecules in the amphiphilic agents and the powder.

The surface treatment may thus be performed, for example, by chemical reaction of the amphiphilic agent with the surface of the powder and creation of a covalent bond between the amphiphilic agent and the powder. This method is specifically described in U.S. Pat. No. 4,578,266.

Powders to which the amphiphilic agents covalently or ionically bond are preferably used.

The amphiphilic agents may represent from 0.1% to 50% by weight, preferably from 0.5% to 30% by weight, and more preferably 1% to 10% by weight, relative to the total weight of the surface-treated powders.

It is preferable that the amphiphilic agent comprise at least one hydrophobicized amino acid. The hydrophobicized amino acid may be a glutamic acid derivative or a condensate of at least one glutamic acid derivative and an amino acid.

The glutamic acid derivative may be N-acylated glutamic acid or a salt thereof. As the salt, mention may be made of metal salts, ammonium salts, and onium salts of an organic alkanolamine. As the metal, Na, K, Ba, Zn, Ca, Mg, Fe, Zr, Co, Al, and Ti may be used. As the organic alkanolamine, monoethanolamine, diethanolamine, triethanolamine, 2-amino-2-methylpropanol, 2-amino-2-methyl-1,3-propanediol, and triisopropanolamine may be used. The acyl group bound to the nitrogen atom of the glutamic acid may be derived from a saturated or unsaturated fatty acid having 8 to 22 carbon atoms, such as capric acid, lauric acid, myristic acid, isomyristic acid, palmitic acid, isopalmitic acid, stearic acid, isostearic acid, arachic acid, undecylenic acid, oleic acid, myristic acid, elaidic acid, linolic acid, linoleic acid, arachidonic acid, palm oil fatty acid, beef tallow fatty acid, and resin acid (abietic acid).

The condensate of at least one glutamic acid derivative and an amino acid may be a condensate of N-acylated glutamic acid and an amino acid such as lysine, or a salt thereof. As the salt, mention may be made of metal salts, ammonium salts and onium salts of an organic alkanolamine as mentioned above. Sodium salt is preferable. The acyl group bound to the nitrogen atom of the glutamic acid may be derived from a saturated or unsaturated fatty acid having 8 to 22 carbon atoms as mentioned above. Lauric acid is preferable. Thus, for example, sodium dilauramidoglutamide lysine (Pellicer L-30 marketed by Asahi Kasei Chemicals) is preferable as the above condensate.

The amphiphilic surface treatments of the (c) powder may be chosen from the following treatments:

- a PEG-silicone treatment, for instance, the AQ surface treatment sold by LCW;
- a lauroyllysine treatment, for instance, the LL surface treatment sold by LCW;
- a lauroyllysine dimethicone treatment, for instance, the LL/SI surface treatment sold by LCW;
- a disodium stearoyl glutamate treatment, for instance, the NAI surface treatment sold by Miyoshi;
- a dimethicone/disodium stearoyl glutamate treatment, for instance, the SA/NAI surface treatment sold by Miyoshi;
- a microcrystalline cellulose and carboxymethylcellulose treatment, for instance, the AC surface treatment sold by Daito;
- an acrylate copolymer treatment, for instance, the APD surface treatment sold by Daito;
- a sodium dilauramidoglutamide lysine treatment, for instance, the ASL treatment sold by Daito; and
- a sodium dilauramidoglutamide lysine/isopropyl titanium triisostearate treatment, for instance, the ASL treatment sold by Daito.

Amphiphilic agent(s) can be bound to particles ionically with a metal salt or hydroxide whose metal can be selected from Mg, Al, Ca, and Zn, for instance, aluminum hydroxide and magnesium chloride.

A treatment using disodium stearoyl glutamate (and) aluminum hydroxide is more preferable.

Other treatments using a sodium dilauramidoglutamide lysine, or a sodium dilauramidoglutamide lysine/isopropyl titanium triisostearate, are also more preferable.

In one embodiment of the present invention, the (c) powder itself may function as a cosmetic active agent such as opacifiers, pearlescent agents, feel modifiers, skin protectants, matting agents, friction enhancers, slip agents, conditioning agents, exfoliants, odor absorbers, coloring agents and cleaning enhancers.

(UV Filter)

The UV filter can be selected from the group consisting of an inorganic UV filter, an organic UV filter, and a mixture thereof.

(Inorganic UV Filter)

The inorganic UV filter used for the present invention may be active in the UV-A and/or UV-B region. The inorganic UV filter may be hydrophilic and/or lipophilic. The inorganic UV filter is preferably insoluble in solvents such as water and ethanol commonly used in cosmetics.

It is preferable that the inorganic UV filter be in the form of a fine particle such that the mean (primary) particle diameter thereof ranges from 1 nm to 50 nm, preferably 5 nm to 40 nm, and more preferably 10 nm to 30 nm. The mean (primary) particle size or mean (primary) particle diameter here is an arithmetic mean diameter.

The inorganic UV filter can be selected from the group consisting of silicon carbide, metal oxides which may or may not be coated, and mixtures thereof.

Preferably, the inorganic UV filters may be selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide or cerium oxide, 45 which are all UV photoprotective agents that are well known per se. Preferably, the inorganic UV filters may be selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl)Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes, and polyalkylhydrosiloxanes. More preferably still, the silicones are selected from the group consisting of octyltrimethylsilanes, polydimethylsiloxanes, and polymethylhydrosiloxanes.

Of course, the inorganic UV filters made of metal oxides may, before their treatment with silicones, have been treated with other surfacing agents, in particular, with cerium oxide, alumina, silica, aluminum compounds, silicon compounds, or their mixtures.

The coated inorganic UV filter may have been prepared by subjecting the inorganic UV filter to one or more surface treatments of a chemical, electronic, mechanochemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated with:

silica, such as the product "Sunveil" from Ikeda;

silica and iron oxide, such as the product "Sunveil F" from Ikeda;

silica and, alumina, such as the products "Microtitanium Dioxide MT 500 SA" from Tayca, "Tioveil" from Tioxide, and "Mirasun TiW 60" from Rhodia;

alumina, such as the products "Tipaque TTO-55 (B)" and "Tipaque TTO-55 (A)" from Ishihara, and "UVT 14/4" from Kemira;

alumina and aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck;

alumina and aluminum laurate, such as the product "Microtitanium Dioxide MT 100 S" from Tayca;

- iron oxide and iron stearate, such as the product "Microtitanium Dioxide MT 100 F" from Tayca;
- zinc oxide and zinc stearate, such as the product "BR351" from Tayca;
- silica and alumina and treated with a silicone, such as the products "Microtitanium Dioxide MT 600 SAS", "Microtitanium Dioxide MT 500 SAS", and "Microtitanium Dioxide MT 100 SAS" from Tayca;
- silica, alumina, and aluminum stearate and treated with a silicone, such as the product "STT-30-DS" from Titan Kogyo;
- silica and treated with a silicone, such as the product "UV-Titan X 195" from Kemira;
- alumina and treated with a silicone, such as the products "Tipaque TTO-55. (S)" from Ishihara or "UV Titan M 262" from Kemira;
- triethanolamine, such as the product "STT-65-S" from Titan Kogyo;
- stearic acid, such as the product "Tipaque TTO-55 (C)" from Ishihara; or sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter: Stearic acid (and) Aluminum Hydroxide (and) $TiO_2$, such as the product "MT-100 TV" from Tayca, with a mean primary particle diameter of 15 nm;

Dimethicone (and) Stearic Acid (and) Aluminum Hydroxide (and) $TiO_2$, such as the product "SA-TTO-S4" from Miyoshi Kasei, with a mean primary particle diameter of 15 nm; Silica (and) $TiO_2$, such as the product "MT-100 WP" from Tayca, with a mean primary particle diameter of 15 nm;

Dimethicone (and) Silica (and) Aluminum Hydroxide (and) $TiO_2$, such as the product "MT-Y02" and "MT-Y-110 M3S" from Tayca, with a mean primary particle diameter of 10 nm;

Dimethicone (and) Aluminum Hydroxide (and) $TiO_2$, such as the product "SA-TTO-S3" from Miyoshi Kasei, with a mean primary particle diameter of 15 nm;

Dimethicone (and) Alumina (and) $TiO_2$, such as the product "UV TITAN M170" from Sachtleben, with a mean primary particle diameter of 15 nm; and Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS", and by Tioxide under the trademark "Tioveil AQ".

The uncoated zinc oxide pigments are, for example:

those marketed under the trademark "Z-cote" by Sunsmart;

those marketed under the trademark "Nanox" by Elementis; and those marketed under the trademark "Nanogard WCD 2025" by Nanophase Technologies.

The coated zinc oxide pigments are, for example:

those marketed under the trademark "Oxide Zinc CS-5" by Toshiba (ZnO coated with polymethylhydrosiloxane);

those marketed under the trademark "Nanogard Zinc-Oxide FN" by Nanophase Technologies (as a 40% dispersion in Finsolv TN, $C_{12}$-$C_{15}$ alkyl benzoate);

those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);

those marketed under the trademark "NFD Ultrafine ZnO" by Daikin (ZnO coated with phosphate of perfluoroalkyl and a copolymer based on perfluoroalkylethyl as a dispersion in cyclopentasiloxane);

those marketed under the trademark "SPD-Z1" by Shin-Etsu (ZnO coated with a silicone-grafted acrylic polymer dispersed in cyclodimethylsiloxane);

those marketed under the trademark "Escalol Z100" by ISP (alumina-treated ZnO dispersed in an ethylhexyl methoxycinnamate/PVP-hexadecene copolymer/methicone mixture);

those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica, and with glycerol, such as the product "M 211" marketed by Kemira.

Coated inorganic UV filters are preferable, because the UV filtering effects of the inorganic UV filters can be enhanced. In addition, the coating(s) may help uniformly or homogeneously disperse the UV filters in the composition according to the present invention.

(Organic UV Filter)

The organic UV filter used for the present invention may be active in the UV-A and/or UV-B region. The organic UV filter may be hydrophilic and/or lipophilic.

The organic UV filter may be solid or liquid (as long as at least one inorganic or organic solid UV filter is used together therewith). The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadiene compounds; guaiazulene and derivatives thereof; rutin and derivatives thereof; and mixtures thereof.

Mention may be made, as examples of the organic UV filter(s), of those denoted below under their INCI names, and mixtures thereof.

Anthranilic compounds: Menthyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; benzophenone-12, and n-hexyl 2-(4-diethylamino-2-hydroxybenzoyl)benzoate (UVINUL A+ by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVINUL T150» by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184 and EP-893,119, and Drometrizole trisiloxane, marketed under the trademark "Silatrizole" by Rhodia Chimie or "Mexoryl XL" by L'Oreal, as represented below.

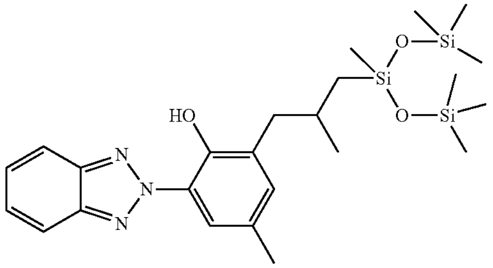 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1(dimethylpropyl) benzoxazol-2-yl-(4-phenyl)imino]-6-(2-ethylhexyl) imino-1,3,5-triazine, marketed under the trademark Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

It is preferable that the organic UV filter(s) be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,1'-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl) imino-1,3,5-triazine, camphor benzylkonium methosulfate and mixtures thereof.

It is preferable that the (c) powder be selected from inorganic pigments, inorganic fillers, UV filters and mixtures thereof, and more preferably from titanium dioxide particles, silica particles and mixtures thereof.

It is even more preferable that the titanium dioxide be in pigment-grade. For example, the titanium dioxide preferably has an average particle size of more than 50 nm, more preferably more than 70 nm, and even more preferably more than 100 nm. The average particle size may be number-average particle size which can be measured by dynamic light scattering with, for example, Nicomp Z380.

The amount of the (c) powder(s) in the composition according to the present invention may be from 0.1% by weight or more, preferably 0.5% by weight or more, and more preferably from 1% by weight or more, relative to the total weight of the composition.

The amount of the (c) powder(s) in the composition according to the present invention may be from 25% by weight or less, preferably from 20% by weight or less, and more preferably from 15% by weight or less, relative to the total weight of the composition.

The amount of the (c) powder(s) in the composition according to the present invention may be from 0.1% to 25% by weight, preferably from 0.5% to 20% by weight, and more preferably from 1% to 15% by weight, relative to the total weight of the composition.

[Polyol]

The composition according to the present invention includes (d) at least one polyol. Two or more different types of (d) polyols may be used in combination. Thus, a single type of (d) polyol or a combination of different types of (d) polyols may be used.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acyl group or a carbonyl group.

The polyols used in the present invention are liquid at ambient temperature such as 25° C. under atmospheric pressure (760 mmHg or 105 Pa).

The polyol may be a $C_2$-$C_{24}$ polyol, preferably a $C_2$-$C_9$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, $C_6$-$C_{24}$ polyethyleneglycol, 1,3-propanediol, 1,4-butanediol, and 1,5-pentanediol.

It is preferable that the polyol be selected from the group consisting of glycerin, ethyleneglycol, polyethyleneglycol, propyleneglycol, dipropyleneglycol, butyleneglycol, pentyleneglycol, hexyleneglycol and mixtures thereof.

The amount of the (d) polyol(s) in the composition according to the present invention may be from 0.1% by weight or more, preferably 0.5% by weight or more, and more preferably from 1% by weight or more, relative to the total weight of the composition.

The amount of the (d) polyol(s) in the composition according to the present invention may be from 20% by weight or less, preferably from 15% by weight or less, and more preferably from 10% by weight or less, relative to the total weight of the composition.

The amount of the (d) polyol(s) in the composition according to the present invention may be from 0.1% to 20% by weight, preferably from 0.5% to 15% by weight, and more preferably from 1% to 10% by weight, relative to the total weight of the composition.

[pH]

The pH of the composition according to the present invention may be from 3 to 9, preferably from 3.5 to 8, and more preferably from 4 to 7.

The pH of the composition may be adjusted by adding at least one alkaline agent and/or at least one acid. The pH of the composition may also be adjusted by adding at least one buffering agent.

[Alkaline Agent]

The composition according to the present invention may comprise at least one alkaline agent. Two or more alkaline agents may be used in combination. Thus, a single type of alkaline agent or a combination of different types of alkaline agents may be used.

The alkaline agent may be an inorganic alkaline agent. It is preferable that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogeno phosphate.

As examples of the inorganic alkaline metal hydroxides, mention may be made of sodium hydroxide and potassium hydroxide. As examples of the alkaline earth metal hydroxides, mention may be made of calcium hydroxide and magnesium hydroxide. As the inorganic alkaline agent, sodium hydroxide is preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof; polymers of basic amino acids and derivatives thereof; urea and derivatives thereof; and guanidine and derivatives thereof.

As examples of the organic alkaline agents, mention may be made of alkanolamines such as mono-, di- and triethanolamine, and isopropanolamine; urea, guanidine and their derivatives; basic amino acids such as lysine, ornithine or arginine; and diamines such as those described in the structure below:

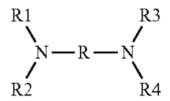

wherein R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical or a $C_1$-$C_4$ hydroxyalkyl radical, which may be exemplified by 1,3-propanediamine and derivatives thereof. Arginine, urea and monoethanolamine are preferable.

The alkaline agent(s) may be used in a total amount of from 0.001% to 10% by weight, preferably from 0.01% to 5% by weight, more preferably from 0.1% to 1% by weight, relative to the total weight of the composition, depending on their solubility.

[Acid]

The composition according to the present invention may comprise at least one acid. Two or more acids may be used in combination. Thus, a single type of acid or a combination of different types of acids may be used.

As the acid, mention may be made of any inorganic or organic acids which are commonly used in cosmetic products. A monovalent acid and/or a polyvalent acid may be used. A monovalent acid such as citric acid, lactic acid, sulfuric acid, phosphoric acid and hydrochloric acid (HCl) may be used. HCl is preferable.

The acid(s) may be used in a total amount of from 0.001% to 10% by weight, preferably from 0.01% to 5% by weight, more preferably from 0.1% to 1% by weight, relative to the total weight of the composition, depending on their solubility.

[Buffering Agent]

The composition according to the present invention may comprise at least one buffering agent. Two or more buffering agents may be used in combination. Thus, a single type of buffering agent or a combination of different types of buffering agents may be used.

As the buffering agent, mention may be made of an acetate buffer (for example, acetic acid+sodium acetate), a phosphate buffer (for example, sodium dihydrogen phosphate+di-sodium hydrogen phosphate), a citrate buffer (for example, citric acid+sodium citrate), a borate buffer (for example, boric acid+sodium borate), a tartrate buffer (for example, tartaric acid+sodium tartrate dihydrate), Tris buffer (for example, tris(hydroxymethyl)aminomethane), and Hepes buffer (4-(2-hydroxyethyl)-1-piperazineethanesulfonic acid).

[Optional Additives]

The composition according to the present invention may comprise, in addition to the aforementioned components, components typically employed in cosmetics, specifically, such as dyes, oils, surfactants, thickeners, organic non-volatile solvents, silicones and silicone derivatives, natural extracts derived from animals or vegetables, waxes, and the like, within a range which does not impair the effects of the present invention.

The composition according to the present invention may comprise the above optional additive(s) in an amount of from 0.01% to 25% by weight, preferably from 0.1% to 20% by weight, and more preferably from 1% to 15% by weight, relative to the total weight of the composition.

In one embodiment, the composition according to the present invention may include at least one oil. Two or more oils may be used in combination. Thus, a single type of oil or a combination of different types of oils may be used.

Herein, the term "oil" is understood to mean a fatty substance which is liquid at ambient temperature (25° C.). The oil(s) may be volatile or non-volatile.

The amount of the oil(s) in the composition according to the present invention may be 40% by weight or less, preferably 30% by weight or less, and more preferably 20% by weight or less, relative to the total weight of the composition.

The amount of the oil(s) in the composition according to the present invention may be 0.1% by weight or more, preferably 1% by weight or more, and more preferably 5% by weight or more, relative to the total weight of the composition.

The amount of the oil(s) in the composition according to the present invention may be from 0.1% to 40% by weight, preferably from 1% to 30% by weight, and more preferably from 5% to 20% by weight, relative to the total weight of the composition.

In one embodiment, the composition according to the present invention may include at least one surfactant. Two or more surfactants may be used in combination. Thus, a single type of surfactant or a combination of different types of surfactants may be used.

The surfactant may be selected from the group consisting of anionic surfactants, amphoteric surfactants, cationic surfactants, and nonionic surfactants. Two or more surfactants may be used in combination. Thus, a single type of surfactant or a combination of different types of surfactants may be used.

It may be preferable that the surfactant be selected from non-ionic surfactants, more preferably from polyglyceryl fatty acid esters, and even more preferably from polyglyceryl fatty acid esters having an HLB value of from 8 to 10.

The amount of the surfactant(s) in the composition according to the present invention may be 15% by weight or less, preferably 10% by weight or less, and more preferably 5% by weight or less, relative to the total weight of the composition.

The amount of the surfactant(s) in the composition according to the present invention may be 0.01% by weight or more, preferably 0.05% by weight or more, and more preferably 0.1% by weight or more, relative to the total weight of the composition.

The amount of the surfactant(s) in the composition according to the present invention may be from 0.01% to 15% by weight, preferably from 0.05% to 10% by weight, and more preferably from 0.1% to 5% by weight, relative to the total weight of the composition.

[Composition]

The composition according to the present invention may be intended to be used as a cosmetic composition. Thus, the cosmetic composition according to the present invention may be intended for application onto a keratin substance. Keratin substance here means a material containing keratin as a main constituent element, and examples thereof include the skin, scalp, nails, lips, hair, and the like. Thus, it is preferable that the cosmetic composition according to the present invention be used for a cosmetic process for the keratin substance, in particular skin.

Thus, the cosmetic composition according to the present invention may be a skin cosmetic composition, preferably a skin care composition or a skin makeup composition, in particular a composition for protecting skin from UV light.

The composition according to the present invention may be in any form such as a solution, a dispersion, an emulsion, a gel, and a paste. If the composition according to the present invention includes at least one oil and/or at least one organic UV filter, the composition according to the present invention may be in the form of an emulsion such as W/O, O/W, W/O/W and O/W/O, preferably, an O/W emulsion.

The composition according to the present invention can be prepared by mixing the above essential and optional ingredients in accordance with any of the processes which are well known to those skilled in the art.

[Film]

The composition according to the present invention can be used for easily preparing a film, in particular a self-healing or self-repairing film.

Thus, the present invention may also relate to a process for preparing a film, preferably a cosmetic film, comprising:

applying onto a substrate, preferably a keratin substrate, more preferably skin, the composition according to the present invention; and drying the composition.

Since the process for preparing a film according to the present invention includes the steps of applying the composition according to the present invention onto a substrate, preferably a keratin substrate, and more preferably skin, and of drying the composition, the process according to the present invention does not need any spin coating or spraying, and therefore, it is possible to easily prepare a film. Thus, the process for preparing a film according to present invention can prepare a film without any special equipment such as spin coaters and spraying machines.

The film may be thin and/or may be transparent, and therefore, may not be easy to perceive. Thus, the film may be used preferably as a cosmetic film.

If the substrate is not a keratin substrate such as skin, the composition according to the present invention may be applied onto a substrate made from any material other than keratin. The materials of the non-keratinous substrate are not limited. Two or more materials may be used in combination. Thus, a single type of material or a combination of different types of materials may be used. In any event, it is preferable that the substrate be flexible or elastic.

If the substrate is not a keratin substrate, it is preferable that the substrate be water-soluble because it is possible to leave the film by washing the substrate with water. As examples of the water-soluble materials, mention may be made of poly(meth) acrylic acids, polyethyleneglycols, polyacrylamides, polyvinylalcohol (PVA), starch, cellulose acetates, and the like. PVA is preferable.

If the non-keratinous substrate is in the form of a sheet, it may have a thickness of more than that of the film according to the present invention, in order to ease the handling of the film attached to the substrate sheet. The thickness of the non-keratinous substrate sheet is not limited, but may be from 1 m to 5 mm, preferably from 10 μm to 1 mm, and more preferably from 50 to 500 μm.

It is more preferable that the film be releasable from the non-keratinous substrate. The mode of release is not limited. Therefore, the film may be peeled from the non-keratinous substrate, or released by the dissolution of the substrate sheet into a solvent such as water.

The present invention may also relate to:

(1) A film, preferably a cosmetic film, prepared by a process comprising:

applying onto a substrate, preferably a keratin substrate, and more preferably skin, the composition according to the present invention; and drying the composition, and (2) A film, preferably a cosmetic film, comprising:

at least one cationic polysaccharide, at least one crosslinker having three or more acid groups or a salt thereof, and optionally at least one anionic polymer.

The above explanations for the ingredients in the composition according to the present invention can apply to the above cationic polysaccharide, the above crosslinker having three or more acid groups or a salt thereof, and the above anionic polymer.

The film thus obtained above may be self-standing. The term "self-standing" here means that the film can be in the form of a sheet and can be handled as an independent sheet without the assistance of a substrate or support. Thus, the term "self-standing" may have the same meaning as "self-supporting".

The film may be used for cosmetic treatments of keratin substances, preferably skin, in particular the face. The film may be in any shape or form. For example, it can be used as a full-face mask sheet, or a patch for a part of the face such as the cheek, nose, and around the eyes.

[Cosmetic Process and Use]

The present invention also relates to:

a cosmetic process for a keratin substance such as skin, comprising: applying to the keratin substance the composition the present invention; and drying the composition to form a cosmetic film on the keratin substance.

The cosmetic process here means non-therapeutic cosmetic method for caring for and/or making up the surface of a keratin substance such as skin.

The above cosmetic film may have cosmetic effects such as absorbing or adsorbing malodor, changing the appearance of a keratin substance such as skin, changing the feel to the touch of the keratin substance, and/or protecting the keratin substance from, for example, dirt or pollutants, due to the properties of the polyion complex particles in the cosmetic film, even if the cosmetic film does not include any cosmetic active ingredient.

In addition, the above cosmetic film may immediately change or modify the appearance of the skin by changing light reflection on the skin and the like, even if the cosmetic film does not include any cosmetic active ingredient. Therefore, it may be possible for the above cosmetic film to conceal skin defects such as pores or wrinkles. Further, the above cosmetic film may immediately change or modify the feel to the touch of the skin by changing the surface roughness on the skin and the like. Furthermore, the above cosmetic film may immediately protect the skin by covering the surface of the skin and shielding the skin, as a barrier, from environmental stresses such as pollutants, contaminants and the like.

The above cosmetic effects can be adjusted or controlled by changing the chemical composition, the thickness and/or the surface roughness of the above cosmetic film.

If the above cosmetic film includes at least one cosmetic active ingredient, the cosmetic film can have cosmetic effects provided by the cosmetic active ingredient(s). For example, if the cosmetic film includes at least one cosmetic active ingredient selected from anti-aging agents, anti-sebum agents, deodorant agents, anti-perspirant agents, whitening agents and a mixture thereof, the cosmetic film can treat the ageing of the skin, absorb sebum on the skin, control odors on the skin, control perspiration on the skin, and/or whiten the skin.

Since the composition according to the present invention includes a powder, if the powder can exert any cosmetic effects such as coloring and/or UV shielding, the above cosmetic film can color or conceal the original color of the keratin substance such as skin and/or limit the darkening of the keratin substance, improve the color and uniformity of the complexion, and/or protect the keratin substance from UV rays.

It may also be possible to apply a makeup cosmetic composition onto the cosmetic film prepared by the present invention.

The present invention may also relate to:

a use of the (d) polyol(s) in a composition comprising a combination of the (a) cationic polysaccharide(s) and the (b) crosslinker having three or more acid groups or a salt thereof, which form a DIC-gel, in order to improve the distribution of the (c) powder in the film formed by the composition. The above explanations for the ingredients (a) to (d) for the composition according to the present invention can apply to those for the use according to the present invention. The use according to the present invention can make the distribution of the (c) powder in the film more even or more uniform, as compared to the case in which no polyol is used in a composition comprising a combination of the ingredients (a) and (b).

EXAMPLES

The present invention will be described in a more detailed manner by way of examples.

However, they should not be construed as limiting the scope of the present invention.

Reference Example (Preparation of DIC-Gel Composed of 2 Components (PQ-67/Phytic acid))

0.79 g of polyquatemium-67 (PQ-67) as a cationic polysaccharide, 0.50 g of a 50 wt % aqueous solution of phytic acid as a cross-linker, 0.15 g of sodium hydroxide, and 98.56 g of water were mixed using a homogenizer. Thus, a stable translucent dispersion was successfully prepared. By evaporating water through heating, this dispersion was concentrated and a DIC-gel was prepared. The final solid concentration was about 10 wt %.

(Self-Healing Property Measurement of DIC-Gel)

The concentrated DIC-gel was cut into two pieces, and these were brought into contact in air at room temperature. After 1 hour, these two pieces adhered to each other.

Also, 1 ml of the DIC-gel translucent dispersion (before evaporating water) was applied onto a glass plate and dried at room temperature for 1 day to prepare a DIC-gel film. The surface of the DIC-gel film was scratched by a toothpick, and measured by confocal microscopy. On the film, a drop of water was poured and left to stand for 30 seconds. After removing the water, the surface was measured again. The trace of the scratch disappeared.

Examples 1 and 2 and Comparative Examples 1 and 2

The following compositions according to Examples 1 and 2 and Comparative Examples 1 and 2, shown in Table 1, were prepared by mixing the components shown in Table 1. The numerical values for the amounts of the components shown in Table 1 are all based on "% by weight" as active raw materials.

TABLE 1

(BB cream)

| | Ex. 1 | Ex. 2 | Comp. Ex. 1 | Comp. Ex. 2 |
|---|---|---|---|---|
| Water | qsp 100 | qsp 100 | qsp 100 | qsp 100 |
| Polyquaternium-67 | 0.43 | 0.344 | 0.43 | — |
| Phytic Acid | 0.18 | 0.144 | 0.18 | — |
| Dipropylene Glycol | 5 | — | — | 5 |
| Pentylene Glycol | — | 5 | — | — |
| Trisodium Ethylenediamine Disuccinate | 0.2 | 0.2 | 0.2 | 0.2 |
| Potassium Cetyl Phosphate | — | — | — | 1 |
| Sodium Cocoyl Sarcosinate | — | — | — | 1 |
| Isocetyl Stearate | 2 | 2 | 2 | 2 |
| Diisopropyl Sebacate | 2 | 2 | 2 | 2 |
| Glyceryl Stearate (and) PEG-100 Stearate | 1.5 | 1.5 | 1.5 | 1.5 |
| Cetyl Alcohol | 1.7 | 1.7 | 1.7 | 1.7 |
| Behenyl Alcohol | 0.8 | 0.8 | 0.8 | 0.8 |
| Polyglyceryl-4 Isostearate | 1 | 1 | 1 | 1 |
| Octocrylene | 4 | 4 | 4 | 4 |
| Homosalate | 5 | 5 | 5 | 5 |
| Diethylamino Hydroxybenzoyl Hexyl Benzoate | 0.5 | 0.5 | 0.5 | 0.5 |
| Butyl Methoxydibenzoylmethane | 4 | 4 | 4 | 4 |
| Ethylhexyl Triazone | 2 | 2 | 2 | 2 |
| Polyhydroxystearic Acid | 0.4 | 0.4 | 0.4 | 0.4 |
| Titanium Dioxide | 4.5 | 4.5 | 4.5 | 4.5 |
| Titanium Dioxide (and) Alumina (and) Isopropyl Titanium Triisostearate | 5.67 | 4.74 | 5.67 | 5.67 |
| Iron Oxides (and) Isopropyl Titanium Triisostearate | 0.63 | 0.48 | 0.63 | 0.63 |
| Aluminum Starch Octenylsuccinate | 1.5 | 1.5 | 1.5 | 1.5 |
| Phenoxyethanol | 0.6 | 0.6 | 0.6 | 0.6 |
| Tocopherol | 0.1 | 0.1 | 0.1 | 0.1 |
| Fragrance | 0.35 | 0.35 | 0.35 | 0.35 |
| Ethanol | 4.9 | 4.9 | 4.9 | 4.9 |
| Color Evenness | 1.5 | 1 | 3 | 1 |
| Friction Resistance SPF (%) | 112 | 101 | 88 | 50 |

[Process]

The ingredients for the oil phase were heated so that they melted and mixed to form a melted oil phase. Titanium dioxide and iron oxide were added to the melted oil phase. The melted oil phase was added to an aqueous phase including water and the cationic polymer (polyquatemnium-67), and dispersed or emulsified at high temperature. Then, the other ingredients were added and mixed at room temperature to form a homogenous cream.

[Evaluations]

(Color Evenness)

60 mg each of the compositions according to Examples 1 and 2 and Comparative Examples 1 and 2 was applied onto the forearm (5×5 $cm^2$) by tapping with a finger for 1 minute, followed by drying at room temperature for 2 minutes. Then, the composition was spread with the same finger. The color evenness of the spread composition was evaluated by panelists in accordance with the scoring from 1 (even) to 3 (uneven).

The results of the evaluation are shown in Table 1.

The comparison of Examples 1 and 2 with Comparative Example 1 demonstrates that the addition of polyol under the presence of a combination of a cationic polysaccharide and a crosslinker having three or more acid groups or a salt thereof, which forms a DIC-gel, can improve color evenness.

(Friction Resistance SPF)

The same amount of each of the compositions according to Examples 1 and 2 and Comparative Examples 1 and 2 was applied onto a clear polyester sheet (thickness: 2 mm, BYK) with a 10 micrometer steel bar coater (Elecometer 4340, Speed 3) under 1 kg weight. The applied composition was left for 30 minutes at room temperature. The initial SPF of the composition was measured with an SPF analyzer UV 2000. Friction was then applied with a 10 micrometer steel bar coater (Elecometer 4340, Speed 3) under no weight. The steel bar has a wire wound around the bar to form concaves with a depth of 10 microns and a convex with a height of 10 microns. Next, the SPF value of the composition after the friction was measured with an SPF analyzer UV 2000. The friction resistance SPF (%) was calculated based on the following formula: SPF value after friction/initial SPF value.

The results of the calculation are shown in Table 1.

It should be noted that the SPF value after friction of Example 1 was higher than the initial SPF value thereof, which means that the initial distribution of the $TiO_2$ particles in the film of the composition according to Example 1 was more homogenized by the friction such that the SPF value increased after the friction.

It should also be noted that the SPF value after friction of Example 2 was almost the same as the initial SPF value thereof, which means that the initial distribution of the $TiO_2$ particles in the film of the composition according to Example 2 was not influenced by the friction such that the initial SPF value was maintained.

The comparison of Examples 1 and 2 with Comparative Example 1 demonstrates that the addition of polyol under the presence of a combination of a cationic polysaccharide and a crosslinker having three or more acid groups or a salt thereof, which forms a DIC-gel, can improve the friction resistance SPF.

On the other hand, the comparison of Example 1 with Comparative Example 2 demonstrates that the lack of a cationic polysaccharide and a crosslinker having three or more acid groups or a salt thereof, which forms a DIC-gel, makes the friction resistance SPF worse. It is understandable that the presence of the DIC-gel formed by the cationic polysaccharide and the crosslinker in the composition according to Example 1 can provide the film of the composition with a self-healing property such that scratches formed by the friction on the film disappeared and the UV shielding effects represented by the SPF value did not decrease (rather, the total UV shielding effects increased due to the greater homogenization of the $TiO_2$ particles due to the friction as explained above), while the composition according to Comparative Example 2 cannot have such self-healing property due to the DIC-gel so that scratches formed due to the friction on the film did not disappear and the total UV shielding effects decreased due to the friction.

Example 3

The following composition according to Example 3, shown in Table 2, were prepared by mixing the components shown in Table 2. The numerical values for the amounts of the components shown in Table 2 are all based on "% by weight" as active raw materials.

TABLE 2

| (UV cream) | |
|---|---|
| Water | qsp 100 |
| Polyquaternium-67 | 0.34 |
| Phytic Acid | 0.14 |
| Pentylene Glycol | 5 |
| Trisodium Ethylenediamine Disuccinate | 0.2 |
| Diisopropyl Sebacate | 5.4 |
| Glyceryl Stearate (and) PEG-100 Stearate | 1.5 |
| Cetyl Alcohol | 1.7 |
| Behenyl Alcohol | 0.5 |
| Synthetic Wax | 1 |
| Polyglyceryl-4 Isostearate | 1 |
| Octocrylene | 6 |
| Homosalate | 5 |
| Diethylamino Hydroxybenzoyl Hexyl Benzoate | 4 |
| Butyl Methoxydibenzoylmethane | 1 |
| Ethylhexyl Triazone | 2.5 |
| Titanium Dioxide | 4.5 |
| Silica | 1 |
| Phenoxyethanol | 0.6 |
| Tocopherol | 0.1 |
| Fragrance | 0.25 |
| Ethanol | 4.9 |

[Process]

The ingredients for the oil phase were heated so that they melted and mixed to form a melted oil phase. Titanium dioxide and iron oxide were added to the melted oil phase. The melted oil phase was added to an aqueous phase including water and the cationic polymer (polyquaternium-67), and dispersed or emulsified at high temperature. Then, the other ingredients were added and mixed at room temperature to form a homogenous cream.

Example 4

The following composition according to Example 4, shown in Table 3, were prepared by mixing the components shown in Table 3. The numerical values for the amounts of the components shown in Table 3 are all based on "% by weight" as active raw materials.

TABLE 3

| (UV milk, shaka-shaka type) | |
|---|---|
| OCTOCRYLENE | 3 |
| DROMETRIZOLE TRISILOXANE | 0.5 |
| ETHYLHEXYL TRIAZONE | 1.5 |
| DIETHYLAMINO HYDROXYBENZOYL HEXYL BENZOATE | 3 |
| HOMOSALATE | 7 |
| DIISOPROPYL SEBACATE | 5 |
| DICAPRYLYL CARBONATE | 5 |
| POLY C10-30 ALKYL ACRYLATE | 0.2 |
| POLYGLYCERYL-6 POLYRICINOLEATE | 1 |
| CETYL PEG/PPG-10/1 DIMETHICONE | 1 |
| PEG10 DIMETHICONE | 0.5 |
| ISOSTEARIC ACID | 1 |
| DISTEARDIMONIUM HECTORITE (and) PROPYLENE CARBONATE | 2 |
| TITANIUM DIOXIDE | 6.2 |
| WATER | 20 |
| POLYQUATERNIUM-67 | 0.17 |
| PHYTIC ACID | 0.07 |
| PROPYLENE GLYCOL | 3 |
| PENTYLENE GLYCOL | 3 |
| TRISODIUM ETHYLENEDIAMINE DISUCCINATE | 0.1 |
| ISOHEXADECANE | 5 |
| C15-19 ALKANE | qsp 100 |
| DIMETHICONE | 9 |
| TOCOPHEROL | 0.1 |
| DIMETHICONE (and) DIMETHICONE/VINYL DIMETHICONE CROSSPOLYMER | 2 |
| SILICA | 5.5 |
| CELLULOSE | 4 |
| FRAGRANCE | 0.25 |
| ETHANOL | 8 |

[Process]

The ingredients for the oil phase were heated so that they melted and mixed to form a melted oil phase. Titanium dioxide and iron oxide were added to the melted oil phase. The melted oil phase was added to an aqueous phase including water and the cationic polymer (polyquatemnium-67), and dispersed at high temperature. Then, the other ingredients were added and mixed at room temperature to form a homogenous milk.

Example 5 and Comparative Example 3

TABLE 4

(Liquid foundation)

| INCI name | Ex. 5 | Comp. Ex. 3 |
|---|---|---|
| WATER | 42.32 | 42.80 |
| POLYQUATERNIUM-67 | 0.34 | 0.00 |
| PHYTIC ACID | 0.14 | 0.00 |
| GLYCERIN | 3.00 | 3.00 |
| PENTYLENE GLYCOL | 5.00 | 5.00 |
| CAPRYLYL GLYCOL | 0.30 | 0.30 |
| TRISODIUM ETHYLENEDIAMINE DISUCCINATE | 0.20 | 0.20 |
| GLYCERYL STEARATE (and) PEG-100 STEARATE | 1.50 | 1.50 |
| CETYL ALCOHOL | 1.70 | 1.70 |
| POLYGLYCERYL-4 ISOSTEARATE | 1.00 | 1.00 |
| BEHENYL ALCOHOL | 0.80 | 0.80 |
| DROMETRIZOLE TRISILOXANE | 1.00 | 1.00 |
| HOMOSALATE | 5.00 | 5.00 |
| BUTYL METHOXYDIBENZOYLMETHANE | 4.00 | 4.00 |
| ETHYLHEXYL TRIAZONE | 2.00 | 2.00 |
| DIETHYLAMINO HYDROXYBENZOYL HEXYL BENZOATE | 0.50 | 0.50 |
| TITANIUM DIOXIDE (and) ALUMINA (and) ISOPROPYL TITANIUM TRIISOSTEARATE | 11.00 | 11.00 |
| IRON OXIDES (and) ISOPROPYL TITANIUM TRIISOSTEARATE | 0.15 | 0.15 |

TABLE 4-continued (Liquid foundation)

| INCI name | Ex. 5 | Comp. Ex. 3 |
|---|---|---|
| IRON OXIDES (and) ISOPROPYL TITANIUM TRIISOSTEARATE | 0.90 | 0.90 |
| IRON OXIDES (and) ISOPROPYL TITANIUM TRIISOSTEARATE | 0.05 | 0.05 |
| SILICA (and) METHICONE | 2.00 | 2.00 |
| TALC (and) METHICONE | 3.00 | 3.00 |
| OCTYLDODECYL MYRISTATE | 6.00 | 6.00 |
| OCTOCRYLENE | 2.00 | 2.00 |
| POLYHYDROXYSTEARIC ACID | 0.40 | 0.40 |
| PHENOXYETHANOL | 0.50 | 0.50 |
| TOCOPHEROL | 0.20 | 0.20 |
| ETHANOL | 5.00 | 5.00 |
| TOTAL | 100.00 | 100.00 |

[Process]

The ingredients for the oil phase were heated so that they melted and mixed to form a melted oil phase. Titanium dioxide and iron oxide were added to the melted oil phase. The melted oil phase was added to an aqueous phase including water and the cationic polymer (polyquatemnium-67), and dispersed at high temperature. Then, the other ingredients were added and mixed at room temperature to form a homogenous liquid foundation.

[Evaluation]

(Non-Transfer Property)

Each of the compositions according to Example 5 and Comparative Example 3 was applied on a substrate. The applied composition on each substrate was put on a paper. Non-transfer was evaluated to observe the transfer of the composition to the paper. As a result, the composition according to Example 5 showed better non-transfer effect than that according to Comparative Example 3.

The invention claimed is:

1. A composition, comprising, in at least one physiologically acceptable volatile medium:

(a) at least one cationic polysaccharide;

(b) at least one crosslinker having three or more acid groups or a salt thereof selected from phytic acid and salts thereof;

(c) at least one powder; and (d) at least one polyol selected from the group consisting of glycerin, ethyleneglycol, polyethyleneglycol, propyleneglycol, dipropyleneglycol, butyleneglycol, pentyleneglycol hexyleneglycol and mixtures thereof, wherein the amount of the (a) cationic polysaccharide(s) in the composition is from 0.01% to 5% by weight, the amount of the (b) crosslinker(s) having three or more acid groups or a salt(s) thereof in the composition is from 0.001% to 5% by weight, the amount of the (c) powder(s) in the composition is from 0.1% to 25% by weight, relative to the total weight of the composition, the amount of the (d) polyol(s) in the composition is from 1% to 10% by weight, relative to the total weight of the composition, the (a) cationic polysaccharide(s) and the (b) crosslinker(s) having three or more acid groups or a salt thereof form a dynamically and ionically crosslinked gel, and the (c) powder is insoluble in the physiologically acceptable volatile medium.

2. The composition according to claim 1, wherein the (a) cationic polysaccharide is selected from cationic cellulose polymers.

3. The composition according to claim 1, wherein the (a) cationic polysaccharide has at least one quaternary ammonium group.

4. The composition according to claim 1, wherein the (a) cationic polysaccharide is selected from the group consisting of polyquaternium-4, polyquaternium-10, polyquaternium-24, polyquaternium-67, and a mixture thereof.

5. The composition according to claim 1, wherein the amount of the (a) cationic polysaccharide(s) in the composition is from 0.05% to 5% by weight, relative to the total weight of the composition.

6. The composition according to claim 1, wherein the amount of the (b) crosslinker(s) having three or more acid groups or a salt(s) thereof in the composition is from 0.05% to 5% by weight, relative to the total weight of the composition.

7. The composition according to claim 1, wherein the (c) powder is selected from pigments, fillers, UV filters and mixtures thereof.

8. The composition according to claim 1, wherein the amount of the (c) powder(s) in the composition is from 0.5% to 20% by weight, relative to the total weight of the composition.

9. The composition according to claim 1, wherein the (d) polyol is selected from the group consisting of dipropyleneglycol, butyleneglycol and a mixture thereof.

10. The composition according to claim 1, wherein the composition is a skin cosmetic composition.

11. A cosmetic process for skin, comprising applying to the skin the composition according claim 1; and drying the composition to form a cosmetic film on the skin.

12. The composition according to claim 1, wherein the amount of the (c) powder(s) in the composition is from 1% to 15% by weight, relative to the total weight of the composition.

* * * * *